United States Patent
Horner et al.

(10) Patent No.: US 11,957,403 B2
(45) Date of Patent: *Apr. 16, 2024

(54) APPARATUS FOR PERFORMING AN ELECTROSURGICAL PROCEDURE

(71) Applicant: Covidien LP, Mansfield, MA (US)

(72) Inventors: Glenn A. Horner, Boulder, CO (US); James D. Allen, IV, Broomfield, CO (US)

(73) Assignee: Covidien LP, Mansfield, MA (US)

( * ) Notice: Subject to any disclaimer, the term of this patent is extended or adjusted under 35 U.S.C. 154(b) by 94 days.

This patent is subject to a terminal disclaimer.

(21) Appl. No.: 17/189,606

(22) Filed: Mar. 2, 2021

(65) Prior Publication Data

US 2021/0177499 A1    Jun. 17, 2021

Related U.S. Application Data

(60) Continuation of application No. 16/556,619, filed on Aug. 30, 2019, now Pat. No. 11,234,758, which is a
(Continued)

(51) Int. Cl.
*A61B 18/14* (2006.01)
*A61B 17/29* (2006.01)
(Continued)

(52) U.S. Cl.
CPC .......... *A61B 18/1445* (2013.01); *A61B 17/29* (2013.01); *A61B 17/295* (2013.01);
(Continued)

(58) Field of Classification Search
CPC ... A61B 17/27; A61B 17/295; A61B 17/2947; A61B 18/085; A61B 18/1445;
(Continued)

(56) References Cited

U.S. PATENT DOCUMENTS 3,920,021 A    11/1975  Hiltebrandt
4,005,714 A    2/1977   Hiltebrandt
(Continued)

FOREIGN PATENT DOCUMENTS

DE    2415263 A1   10/1975
DE    02514501 A1  10/1976
(Continued)

OTHER PUBLICATIONS

Michael Choti, "Abdominoperineal Resection with the LigaSure Vessel Sealing System and LigaSure Atlas 20 cm Open Instrument" Innovations That Work, Jun. 2003.
(Continued)

*Primary Examiner* — Michael F Peffley
(74) *Attorney, Agent, or Firm* — Carter, DeLuca & Farrell LLP

(57) ABSTRACT

A surgical instrument is provided and includes a housing having a shaft. An end effector assembly is operatively connected to a distal end of the shaft and has a pair of first and second jaw members that are movable relative to one another. A drive assembly operably couples to a handle assembly associated with the housing and is configured to impart movement of a respective jaw member when the handle assembly is actuated. A spring component operably associated with each of the jaw members is configured to provide a sealing force at the jaw members.

19 Claims, 9 Drawing Sheets

Related U.S. Application Data continuation of application No. 15/338,510, filed on Oct. 31, 2016, now Pat. No. 10,426,544, which is a division of application No. 14/083,696, filed on Nov. 19, 2013, now Pat. No. 9,480,522, which is a division of application No. 12/792,038, filed on Jun. 2, 2010, now Pat. No. 8,585,736.

(51) Int. Cl.
  *A61B 17/295* (2006.01)
  *A61B 18/08* (2006.01)
  A61B 17/00 (2006.01)
  A61B 18/00 (2006.01)

(52) U.S. Cl.
  CPC .. *A61B 18/085* (2013.01); *A61B 2017/00398* (2013.01); *A61B 2017/00539* (2013.01); *A61B 2017/00544* (2013.01); *A61B 2017/2902* (2013.01); *A61B 2017/2936* (2013.01); *A61B 2018/00589* (2013.01); *A61B 2018/00595* (2013.01); *A61B 2018/00601* (2013.01); *A61B 2018/0063* (2013.01)

(58) Field of Classification Search
  CPC .......... A61B 2017/00398; A61B 2017/00539; A61B 2017/00544; A61B 2017/2902; A61B 2017/2936; A61B 2017/00589; A61B 2017/00595; A61B 2017/00601; A61B 2017/0063; A61B 2017/2932; A61B 2017/2033; A61B 2017/2916; A61B 2017/2919; A61B 2017/2939
  See application file for complete search history.

(56) References Cited

U.S. PATENT DOCUMENTS

| | | |
|---|---|---|
| D263,020 S | 2/1982 | Rau, III |
| D295,893 S | 5/1988 | Sharkany et al. |
| D295,894 S | 5/1988 | Sharkany et al. |
| 4,819,633 A | 4/1989 | Bauer et al. |
| 5,133,727 A | 7/1992 | Bales et al. |
| 5,238,002 A | 8/1993 | Devlin et al. |
| 5,241,968 A | 9/1993 | Slater |
| 5,250,056 A | 10/1993 | Hasson |
| D348,930 S | 7/1994 | Olson |
| 5,419,339 A * | 5/1995 | Palmer .................. A61B 10/06 606/205 |
| 5,454,378 A | 10/1995 | Palmer et al. |
| 5,535,754 A | 7/1996 | Doherty |
| 5,582,617 A | 12/1996 | Klieman et al. |
| D384,413 S | 9/1997 | Zlock et al. |
| 5,666,965 A | 9/1997 | Bales et al. |
| 5,810,876 A | 9/1998 | Kelleher |
| D424,694 S | 5/2000 | Tetzlaff et al. |
| D425,201 S | 5/2000 | Tetzlaff et al. |
| 6,083,150 A | 7/2000 | Aznoian et al. |
| 6,106,543 A | 8/2000 | Esser |
| 6,264,617 B1 * | 7/2001 | Bales .................... A61B 10/06 600/564 |
| D449,886 S | 10/2001 | Tetzlaff et al. |
| D457,958 S | 5/2002 | Dycus et al. |
| D457,959 S | 5/2002 | Tetzlaff et al. |
| 6,527,785 B2 | 3/2003 | Sancoff et al. |
| 6,767,349 B2 | 7/2004 | Ouchi |
| D493,888 S | 8/2004 | Reschke |
| D496,997 S | 10/2004 | Dycus et al. |
| D499,181 S | 11/2004 | Dycus et al. |
| D509,297 S | 9/2005 | Wells |
| D525,361 S | 7/2006 | Hushka |
| D531,311 S | 10/2006 | Guerra et al. |
| D533,942 S | 12/2006 | Kerr et al. |
| D535,027 S | 1/2007 | James et al. |
| D541,418 S | 4/2007 | Schechter et al. |
| D541,938 S | 5/2007 | Kerr et al. |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| 7,749,222 B2 | 7/2010 | Lu et al. |
| 7,766,910 B2 | 8/2010 | Hixson et al. |
| 7,887,536 B2 | 2/2011 | Johnson et al. |
| 7,918,848 B2 | 4/2011 | Lau et al. |
| 7,947,041 B2 | 5/2011 | Tetzlaff et al. |
| 7,951,150 B2 | 5/2011 | Johnson et al. |
| 8,016,827 B2 | 9/2011 | Chojin |
| 8,112,871 B2 | 2/2012 | Brandt et al. |
| 8,114,122 B2 | 2/2012 | Nau, Jr. |
| 8,133,254 B2 | 3/2012 | Dumbauld et al. |
| 8,162,965 B2 | 4/2012 | Reschke et al. |
| 8,187,273 B2 | 5/2012 | Kerr et al. |
| 8,192,444 B2 | 6/2012 | Dycus |
| 8,226,650 B2 | 7/2012 | Kerr |
| 8,241,284 B2 | 8/2012 | Dycus et al. |
| 8,246,618 B2 | 8/2012 | Bucciaglia et al. |
| 8,251,994 B2 | 8/2012 | McKenna et al. |
| 8,266,783 B2 | 9/2012 | Brandt et al. |
| 8,277,446 B2 | 10/2012 | Heard |
| 8,277,447 B2 | 10/2012 | Garrison et al. |
| 8,282,634 B2 | 10/2012 | Cunningham et al. |
| 8,287,536 B2 | 10/2012 | Mueller et al. |
| 8,292,886 B2 | 10/2012 | Kerr et al. |
| 8,298,232 B2 | 10/2012 | Unger |
| 8,303,586 B2 | 11/2012 | Cunningham et al. |
| 8,323,310 B2 | 12/2012 | Kingsley |
| 8,328,803 B2 | 12/2012 | Regadas |
| 8,343,150 B2 | 1/2013 | Artale |
| 8,343,151 B2 | 1/2013 | Siebrecht et al. |
| 8,357,158 B2 | 1/2013 | McKenna et al. |
| 8,357,159 B2 | 1/2013 | Romero |
| 8,382,754 B2 | 2/2013 | Odom et al. |
| 8,382,792 B2 | 2/2013 | Chojin |
| 8,388,647 B2 | 3/2013 | Nau, Jr. et al. |
| 8,425,511 B2 | 4/2013 | Olson |
| 8,430,876 B2 | 4/2013 | Kappus et al. |
| 8,439,911 B2 | 5/2013 | Mueller |
| 8,469,957 B2 | 6/2013 | Roy |
| 8,480,671 B2 | 7/2013 | Mueller |
| 8,486,107 B2 | 7/2013 | Hinton |
| 8,491,625 B2 | 7/2013 | Horner |
| 8,496,656 B2 | 7/2013 | Shields et al. |
| 8,512,371 B2 | 8/2013 | Kerr et al. |
| 8,556,929 B2 | 10/2013 | Harper et al. |
| 8,568,412 B2 | 10/2013 | Brandt et al. |
| 8,585,736 B2 | 11/2013 | Horner et al. |
| 8,623,017 B2 | 1/2014 | Moses et al. |
| 8,623,276 B2 | 1/2014 | Schmaltz et al. |
| 8,632,539 B2 | 1/2014 | Twomey et al. |
| 8,632,564 B2 | 1/2014 | Cunningham |
| 8,636,761 B2 | 1/2014 | Cunningham et al. |
| 9,480,522 B2 | 11/2016 | Horner et al. |
| 10,166,037 B2 | 1/2019 | Frings |
| 10,426,544 B2 | 10/2019 | Horner et al. |
| 2005/0165429 A1 * | 7/2005 | Douglas ............... A61B 17/122 606/157 |
| 2005/0216036 A1 | 9/2005 | Nakao |
| 2006/0190034 A1 | 8/2006 | Nishizawa et al. |
| 2006/0217697 A1 | 9/2006 | Lau et al. |
| 2006/0235368 A1 | 10/2006 | Oz |
| 2007/0173814 A1 | 7/2007 | Hixson et al. |
| 2007/0260242 A1 | 11/2007 | Dycus et al. |
| 2009/0112206 A1 | 4/2009 | Dumbauld et al. |
| 2009/0198233 A1 | 8/2009 | Chojin |
| 2009/0204114 A1 | 8/2009 | Odom |
| 2010/0069953 A1 | 3/2010 | Cunningham et al. |
| 2010/0094271 A1 | 4/2010 | Ward et al. |
| 2010/0130971 A1 | 5/2010 | Baily |
| 2010/0179543 A1 | 7/2010 | Johnson et al. |
| 2010/0249769 A1 | 9/2010 | Nau, Jr. et al. |
| 2010/0280511 A1 | 11/2010 | Rachlin et al. |
| 2011/0034918 A1 | 2/2011 | Reschke |
| 2011/0046623 A1 | 2/2011 | Reschke |
| 2011/0054468 A1 | 3/2011 | Dycus |

(56) References Cited

U.S. PATENT DOCUMENTS

| | | |
|---|---|---|
| 2011/0054471 A1 | 3/2011 | Gerhardt et al. |
| 2011/0060335 A1 | 3/2011 | Harper et al. |
| 2011/0071523 A1 | 3/2011 | Dickhans |
| 2011/0073594 A1 | 3/2011 | Bonn |
| 2011/0077648 A1 | 3/2011 | Lee et al. |
| 2011/0118736 A1 | 5/2011 | Harper et al. |
| 2011/0190765 A1 | 8/2011 | Chojin |
| 2011/0193608 A1 | 8/2011 | Krapohl |
| 2011/0251605 A1 | 10/2011 | Hoarau et al. |

FOREIGN PATENT DOCUMENTS

| | | | |
|---|---|---|---|
| DE | 2627679 A1 | 1/1977 | |
| DE | 03423356 C2 | 6/1986 | |
| DE | 03612646 A1 | 4/1987 | |
| DE | 8712328 U1 | 2/1988 | |
| DE | 04303882 C2 | 2/1995 | |
| DE | 04403252 A1 | 8/1995 | |
| DE | 19515914 C1 | 7/1996 | |
| DE | 19506363 A1 | 8/1996 | |
| DE | 29616210 U1 | 11/1996 | |
| DE | 19608716 C1 | 4/1997 | |
| DE | 19751106 A1 | 5/1998 | |
| DE | 19738457 A1 | 3/1999 | |
| DE | 19751108 A1 | 5/1999 | |
| DE | 20121161 U1 | 4/2002 | |
| DE | 10045375 C2 | 10/2002 | |
| DE | 202007009317 U1 | 8/2007 | |
| EP | 1177771 A1 | 2/2002 | |
| EP | 1159926 A2 | 3/2003 | |
| JP | 61501068 A | 5/1986 | |
| JP | 65502328 | 3/1992 | |
| JP | 55106 | 1/1993 | |
| JP | 540112 | 2/1993 | |
| JP | 06343644 | 12/1994 | |
| JP | 07265328 | 10/1995 | |
| JP | 08056955 | 3/1996 | |
| JP | 08252263 A | 10/1996 | |
| JP | 09010223 | 1/1997 | |
| JP | 11070124 A | 3/1999 | |
| JP | 11244298 | 9/1999 | |
| JP | 2000102545 A | 4/2000 | |
| JP | 2000342599 A | 12/2000 | |
| JP | 2000350732 A | 12/2000 | |
| JP | 2001008944 A | 1/2001 | |
| JP | 2001029356 A | 2/2001 | |
| JP | 2001128990 A | 5/2001 | |
| SU | 401367 A1 | 10/1973 | |
| WO | 0036986 A1 | 6/2000 | |
| WO | 0154604 A1 | 8/2001 | |
| WO | 2005110264 A2 | 4/2006 | |
| WO | 2008045348 A2 | 4/2008 | |
| WO | 2009039179 A1 | 3/2009 | |

OTHER PUBLICATIONS

Chung et al., "Clinical Experience of Sutureless Closed Hemorrhoidectomy with LigaSure" Diseases of the Colon & Rectum vol. 46, No. Jan. 1, 2003.
Tinkcler L.F., "Combined Diathermy and Suction Forceps", Feb. 6, 1967, British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.
Peterson et al., "Comparison of Healing Process Following Ligation with Sutures and Bipolar Vessel Sealing" Surgical Technology International (2001).
"Electrosurgery: A Historical Overview" Innovations in Electrosurgery; Sales-Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford, "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al. "Extended Left Hemicolectomy Using the LigaSure Vessel Sealing System" Innovations That Work; Sep. 1999.
Kennedy et al. "High-burst-strength, feedback-controlled bipolar vessel sealing" Surgical Endoscopy (1998) 12:876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work,Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report" Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al., "The Mechanism of Blood Vessel Closure by High Frequency Electrocoagulation" Surgery Gynecology & Obstetrics, Oct. 1965 pp. 823-831.
Sampayan et al., "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females". Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room"; Sales/Product Literature 2001.
Bergdahl et al., "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al., "Sutureless Closed Hemorrhoidectomy: A New Technique" Annals of Surgery, vol. 234, No. 1, Jul. 2001, pp. 21-24.
Levy et al., "Update on Hysterectomy-New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.

(56) References Cited

OTHER PUBLICATIONS

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Jrological Surgery" ANZ Journal of Surgery (2001)71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery"; Grand Rounds in Urology 1999 vol. 1 Issue 4 pp. 10-17.
Craig Johnson, "Use of the LigaSure Vessel Sealing System in Bloodless Hemorrhoidectomy"; Innovations That Work, Mar. 2000.
Levy et al. "Use of a New Energy-based Vessel Ligation Device During Vaginal Hysterectomy"; Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford, "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy"; Sales/Product Literature 2000.
Crouch et al. "A Velocity-Dependent Model for Needle Insertion in Soft Tissue"; MICCA 2005; LNCS 3750 pp. 624-632, Dated: 2005.
McLellan et al., "Vessel Sealing for Hemostasis During Pelvic Surgery" Intl Federation of Gynecology and Obstetrics FIGO World Congress 2000, Washington, DC.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Intl Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Intl Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP11168419.7 dated Aug. 8, 2011.
Int'l Search Report EP11168455.1 dated Sep. 26, 2011.
Int'l Search Report EP11168458.5 dated Jul. 21, 2011.
Int'l Search Report EP 12 169753.6 dated Sep. 14, 2012.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/18676 dated Sep. 19, 2003.
Int'l Search Report PCT/US03/28534dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

* cited by examiner

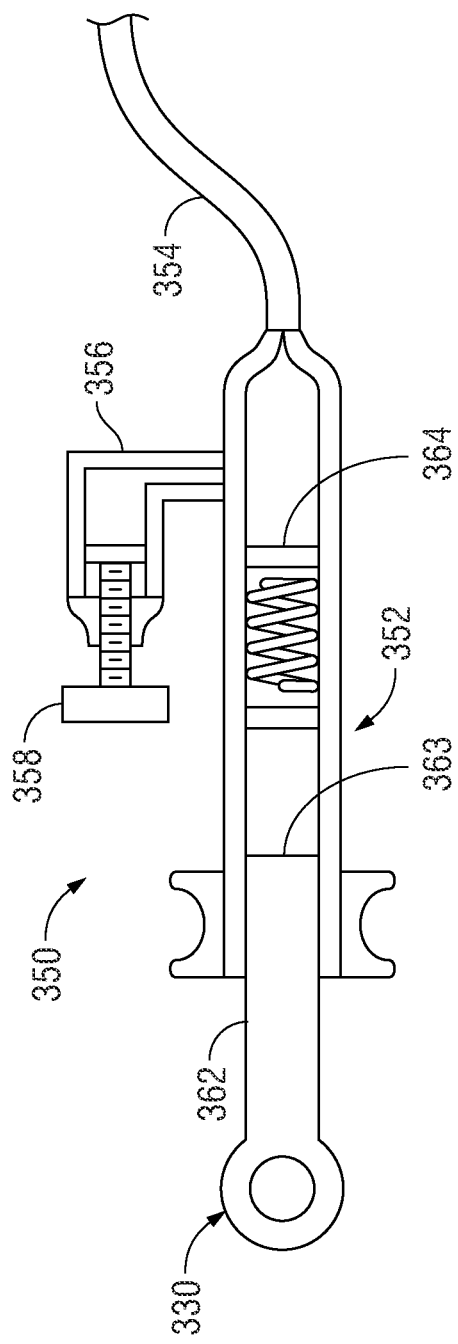
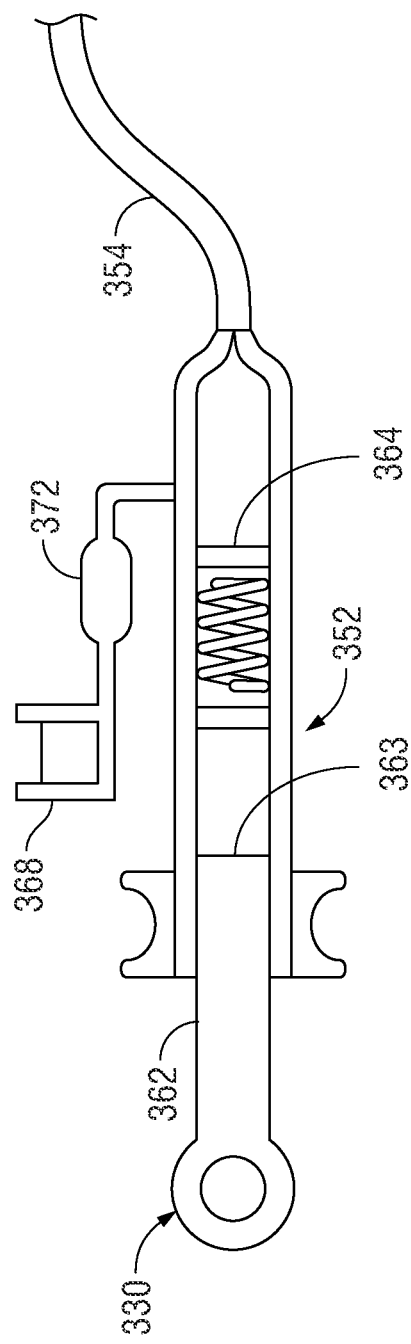

APPARATUS FOR PERFORMING AN ELECTROSURGICAL PROCEDURE

CROSS-REFERENCE TO RELATED APPLICATIONS

This application is a continuation of U.S. patent application Ser. No. 16/556,619, filed on Aug. 30, 2019, now U.S. Pat. No. 11,234,758, which is a continuation of U.S. patent application Ser. No. 15/338,510, filed Oct. 31, 2016, now U.S. Pat. No. 10,426,544, which is a divisional application of U.S. patent application Ser. No. 14/083,696, filed Nov. 19, 2013, now U.S. Pat. No. 9,480,522, which is a divisional application of U.S. patent application Ser. No. 12/792,038, filed on Jun. 2, 2010, now U.S. Pat. No. 8,585,736.

INTRODUCTION

The present disclosure relates to an apparatus for performing an electrosurgical procedure. More particularly, the present disclosure relates to an electrosurgical apparatus including an end effector assembly having a pair of jaw members providing a mechanical advantage at the end effector.

BACKGROUND

Electrosurgical instruments, e.g., electrosurgical forceps (open or closed type), are well known in the medical arts and typically include a housing, a handle assembly, a shaft and an end effector assembly attached to a distal end of the shaft. The end effector includes jaw members configured to manipulate tissue (e.g., grasp and seal tissue). Typically, the electrosurgical forceps utilizes both mechanical clamping action and electrical energy to effect hemostasis by heating the tissue and blood vessels to coagulate, cauterize, seal, cut, desiccate, and/or fulgurate tissue. Typically, one or more driving mechanisms, e.g., a drive assembly including a drive rod, is utilized to cooperate with one or more components operatively associated with the end effector to impart movement to one or both of the jaw members.

In certain instances, to facilitate moving the jaw members from an open position for grasping tissue to a closed position for clamping tissue (or vice versa) such that a consistent, uniform tissue effect (e.g., tissue seal) is achieved, one or more types of suitable devices may be operably associated with the electrosurgical forceps. For example, in some instances, one or more types of springs, e.g., a compression spring, may operably couple to the handle assembly associated with the electrosurgical forceps. In this instance, the spring is typically operatively associated with the drive assembly to facilitate actuation of a movable handle associated with the handle assembly to ensure that a specific closure force between the jaw members is maintained within one or more suitable working ranges.

In certain instances, the shaft may bend or deform during the course of an electrosurgical procedure. For example, under certain circumstances, a clinician may intentionally bend or articulate the shaft to gain desired mechanical advantage at the surgical site. Or, under certain circumstances, the surgical environment may cause unintentional or unwanted bending or flexing of the shaft, such as, for example, in the instance where the shaft is a component of a catheter-based electrosurgical forceps. More particularly, shafts associated with catheter-based electrosurgical forceps are typically designed to function with relatively small jaw members, e.g., jaw members that are configured to pass through openings that are 3mm or less in diameter. Accordingly, the shaft and operative components associated therewith, e.g., a drive rod, are proportioned appropriately. That is, the shaft and drive rod are relatively small.

As can be appreciated, when the shaft is bent or deformed (either intentionally or unintentionally) the frictional losses associated with drive rod translating through the shaft are transferred to the spring in the housing, which, in turn, may diminish, impede and/or prevent effective transfer of the desired closure force that is needed at the jaw members. Moreover, the frictional losses may also lessen the operative life of the spring, which, in turn, ultimately lessens the operative life of the electrosurgical instrument.

An increased mechanical advantage and/or mechanical efficiency with respect to transferring the closure force(s) from the handle assembly to the jaw members may prove advantageous in the relevant art.

SUMMARY

The present disclosure provides an endoscopic forceps. The endoscopic forceps includes a housing having a shaft that extends therefrom defining a longitudinal axis therethrough. An end effector assembly is operatively connected to a distal end of the shaft and has a pair of first and second jaw members. The first and second jaw members movable relative to one another from an open position wherein the first and second jaw members are disposed in spaced relation relative to one another, to a clamping position wherein the first and second jaw members cooperate to grasp tissue therebetween. A drive assembly is operably coupled to a handle assembly associated with the housing. The drive assembly includes a wire having a proximal end and a distal end. The distal end has a split wire configuration including two ends that operably couple to a respective first and second jaw member. The two ends configured to impart movement of a respective jaw member when the handle assembly is actuated. One or both of the two ends forms a spring component that is operably associated with one or both of the first and second jaw members and is configured to bias the jaw members in the open position.

The present disclosure provides an endoscopic forceps that includes a housing having a shaft that extend therefrom and define a longitudinal axis therethrough. An end effector assembly is operatively connected to a distal end of the shaft and has a pair of first and second jaw members that are movable relative to one another. A drive assembly is operably coupled to a handle assembly associated with the housing. The drive assembly includes two wires each including a proximal end that operably couples to the handle assembly and a distal end that operably couples to a respective first and second jaw member. The two wires configured to impart movement of a respective jaw member when the handle assembly is actuated. A center link operably coupled to the first and second jaw members via a respective cam member that is operably disposed within a respective cam slot associated with a respective jaw member.

The present disclosure provides an endoscopic forceps that includes a housing having a shaft that extends therefrom that defines a longitudinal axis therethrough. An end effector assembly is operatively connected to a distal end of the shaft and has a pair of first and second jaw members. The first and second jaw members movable relative to one another from an open position wherein the first and second jaw members are disposed in spaced relation relative to one another, to a clamping position wherein the first and second jaw members cooperate to grasp tissue therebetween. A drive mechanism is operably coupled to a handle assembly associated with the housing and operably coupled to a biasing component operably associated with the first and second jaw members. The biasing component is movable in a plane that is orthogonal to the longitudinal axis and configured to impart movement of the first and second jaw members when the handle assembly is actuated.

The present disclosure also provides an endoscopic forceps that includes a housing having a shaft that extends therefrom that defines a longitudinal axis therethrough. An end effector assembly is operatively connected to a distal end of the shaft and has a pair of first and second jaw members. The first and second jaw members operably disposed in an open position wherein the first and second jaw members are in spaced relation relative to one another. Each of the first and second jaw members including a respective seal plate that is movable from an initial position for positioning tissue therebetween to a subsequent position wherein the respective seal plates cooperate to grasp tissue therebetween. A drive mechanism is operably coupled to a handle assembly associated with the housing and operably coupled to biasing components operably associated with each of the respective seal plates. The biasing components configured to impart movement of the respective seal plates when the handle assembly is actuated. The biasing components operably coupled to the respective seal plates are in the form of respective bellows that are heat activated.

BRIEF DESCRIPTION OF THE DRAWING

Various embodiments of the present disclosure are described hereinbelow with references to the drawings, wherein:

FIG. 5A is a schematic, side view of a hydraulic drive mechanism associated with the endoscopic bipolar forceps depicted in FIG. 4;

FIG. 5B is a schematic, top elevational view of the hydraulic drive mechanism depicted in FIG. 5A;

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1A:
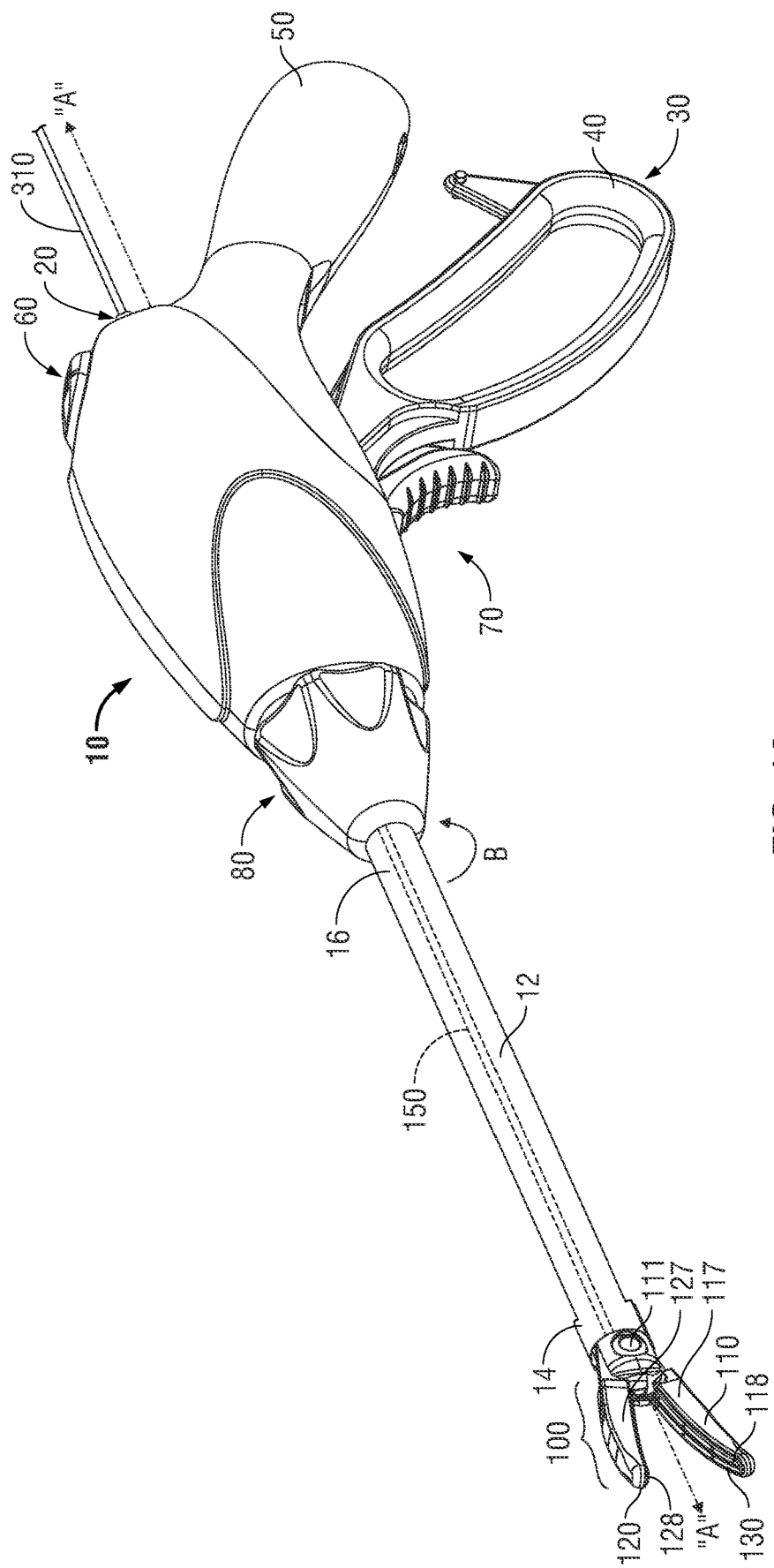
FIG. 1A is a side, perspective view of an endoscopic bipolar forceps showing an end effector assembly including jaw members according to an embodiment of the present disclosure.
Figure 1B:
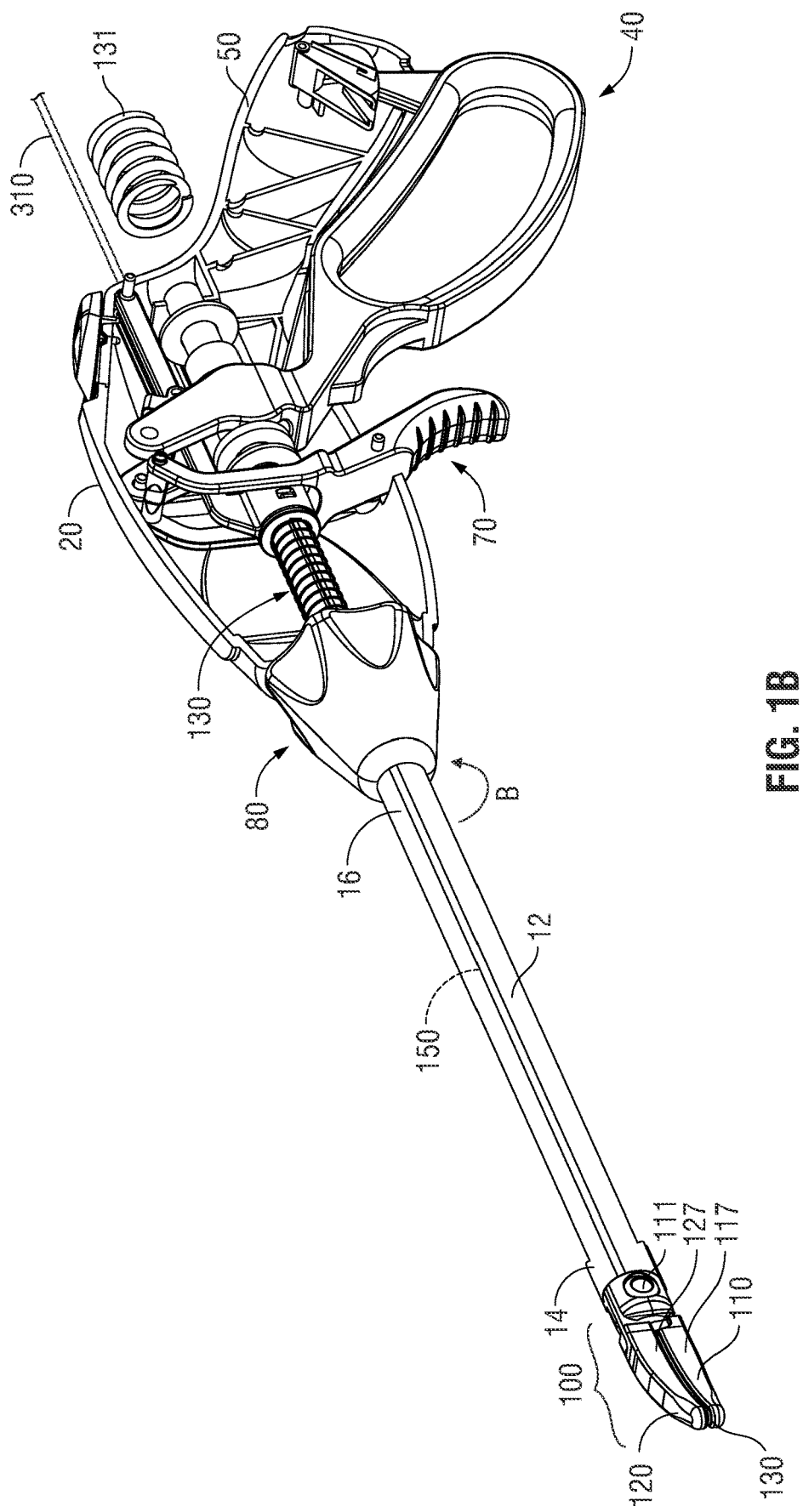
FIG. 1B is a side, perspective view of the endoscopic bipolar forceps depicted in FIG. 1A illustrating internal components associated with a handle assembly associated with the endoscopic bipolar forceps.

With reference to FIGS. 1A and 1B, an illustrative embodiment of an electrosurgical apparatus, e.g., a bipolar forceps 10 is shown. Bipolar forceps 10 is operatively and selectively coupled to an electrosurgical generator (not shown) for performing an electrosurgical procedure. As noted above, an electrosurgical procedure may include sealing, cutting, cauterizing, coagulating, desiccating, and fulgurating tissue all of which may employ RF energy. The generator may be configured for monopolar and/or bipolar modes of operation. The generator may form part of a system (not shown) that may include one or more processors in operative communication with one or more control modules that are executable on the processor. The control module (not explicitly shown) may be configured to instruct one or more modules to transmit electrosurgical energy, which may be in the form of a wave or signal/pulse, via one or more cables (e.g., an electrosurgical cable 310) to one or both seal plates 118, 128.

Bipolar forceps 10 is shown configured for use with various electrosurgical procedures and generally includes a housing 20, electrosurgical cable 310 that connects the forceps 10 to a source of electrosurgical energy (e.g., electrosurgical generator not shown), a handle assembly 30, a rotating assembly 80, a trigger assembly 70, a drive assembly 130 (see FIG. 1B), and an end effector assembly 100 that operatively connects to the drive assembly 130. The drive assembly 130 may be in operative communication with handle assembly 30 for imparting movement of one or both of a pair of jaw members 110, 120 of end effector assembly 100. Conventional drive assemblies typically utilize one or more types of springs, e.g., a compression spring, to facilitate closing the jaw members 110 and 120. For illustrative purposes, a compression spring 131 (see FIG. 1B) is shown separated from the housing 20. End effector assembly 100 includes opposing jaw members 110 and 120 (FIGS. 1A and 1B) that mutually cooperate to grasp, seal and, in some cases, divide large tubular vessels and large vascular tissues.

With continued reference to FIGS. 1A and 1B, forceps 10 includes a shaft 12 that has a distal end 14 configured to mechanically engage the end effector assembly 100 and a proximal end 16 that mechanically engages the housing 20. In the drawings and in the descriptions that follow, the term "proximal," as is traditional, will refer to the end of the forceps 10 which is closer to the user, while the term "distal" will refer to the end that is farther from the user.

Handle assembly 30 includes a fixed handle 50 and a movable handle 40. Fixed handle 50 is integrally associated with housing 20 and handle 40 is movable relative to fixed handle 50. Movable handle 40 of handle assembly 30 is ultimately connected to the drive assembly 130, which together mechanically cooperate to impart movement of one or both of the jaw members 110 and 120 to move from an open position, wherein the jaw members 110 and 120 are disposed in spaced relation relative to one another, to a clamping or closed position, wherein the jaw members 110 and 120 cooperate to grasp tissue therebetween.

For a more detailed description of the bipolar forceps 10 including handle assembly 30 including movable handle 40, rotating assembly 80, trigger assembly 70, drive assembly 130, and electrosurgical cable 310 (including line-feed configurations and/or connections), reference is made to commonly owned U.S. Patent Publication No. 2007/0173814 filed on Nov. 9, 2006.

Figure 2A:
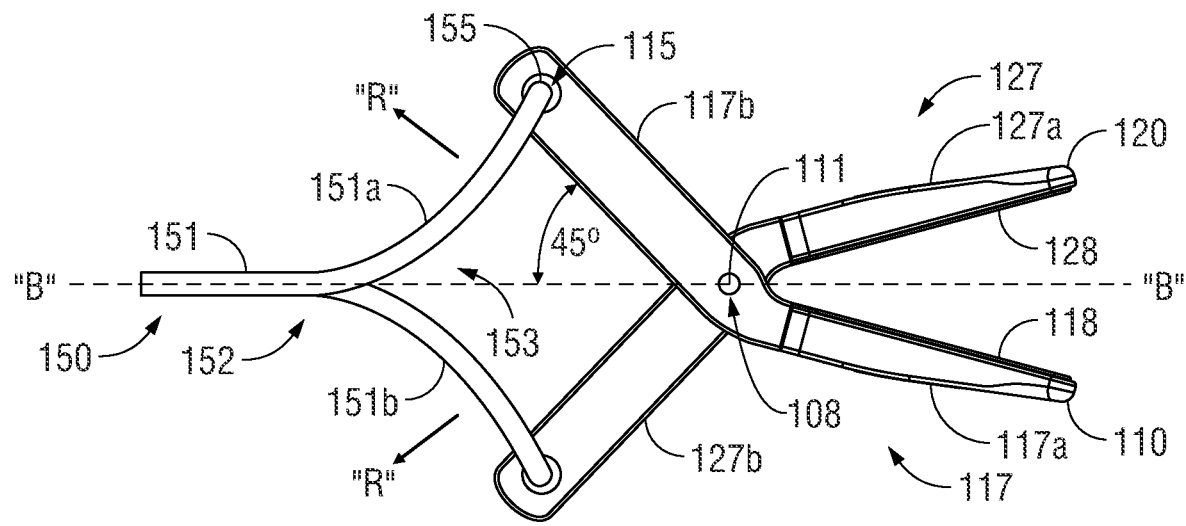
FIGS. 2A and 2B are schematic views of jaw members that may be utilized with the forceps FIGS. 1A and 1B.
Figure 2B:
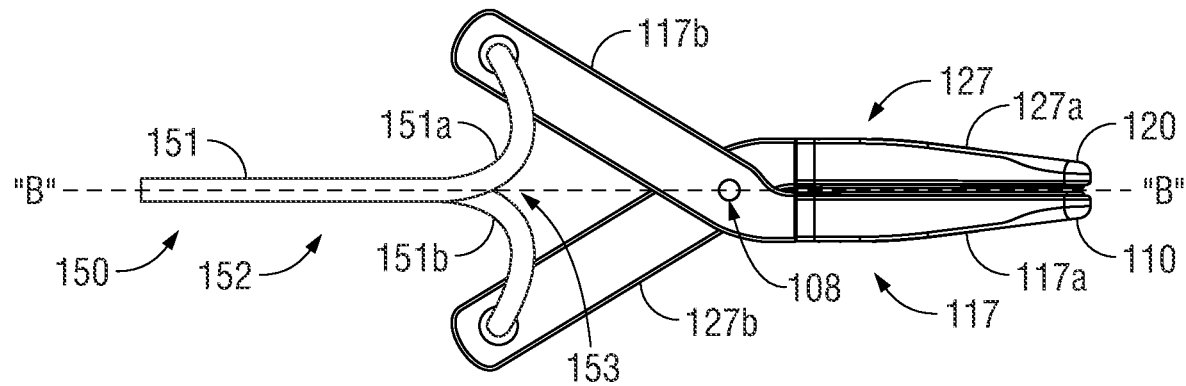

With reference now to FIGS. 2A and 2B, a drive mechanism 150 is operably associated with the drive assembly 130. Drive mechanism 150 may be any suitable drive mechanism including but not limited to a flexible or resilient band, a cable, a wire, etc. In the illustrated embodiment, where the drive mechanism 150 is operatively associated with an endoscopic instrument, the drive mechanism 150 is substantially flexible to accommodate bends typically associated with shaft 12 when the bipolar forceps 10 is remotely actuatable relative to a patient. To this end, the drive mechanism 150 includes a wire 151 of suitable proportion that allows the wire 151 (FIG. 2A) to "bend" or "flex" when the wire 151 is translated, e.g., "pulled" or "pushed." within the shaft 12.

Wire 151 includes a proximal end (not explicitly shown) and a distal end 152. The proximal end operably couples to the drive assembly 130 such that actuation of the movable handle 40 imparts movement of the jaw members 110 and 120. In the embodiment illustrated in FIGS. 2A and 2B, distal end 152 of the wire 151 splits or divides forming a split wire configuration having two generally resilient ends 151a and 151b that operably couple to a respective jaw member 110 and 120, described in greater detail below. The resilient ends 151a and 151b of the split wire configuration bias the jaw members 110 and 120 in an opened configuration and are configured to facilitate movement of the jaw members 110 and 120 when the movable handle 40 is actuated, e.g., moved proximally. More particularly, resilient ends 151a and 151b form a resilient or "spring-like component" 153 (hereinafter simply referred to as spring 153) that is operably associated with each of the jaw members 110 and 120 and configured to bias the jaw members 110 and 120 in the opened position for positioning tissue between the jaw members 110 and 120. Moreover, the resilient ends 151a and 151b are configured to collectively provide the necessary closure or sealing force at the jaw members 110 and 120 when the jaw members 110 and 120 are in the clamping position. More particularly, in the illustrated embodiment, the combination of resilient ends 151a and 151b is configured to provide a spring 153 that is capable of providing a closure force at the jaw members 110 and 120 that is in the range of about 3 kg/cm$^2$ to about 16 kg/cm$^2$ or about 120 pounds per square inch; other suitable ranges are contemplated.

Wire 151 including resilient ends 151a and 151b are configured such that when the movable handle 40 is moved a predetermined distance, the resilient ends 151a and 151b are caused to toward each other, which, in turn, causes the jaw members 110 and 120 to move a corresponding predetermined distance toward each other (or multiple thereof by virtue of one or more known mechanical multipliers, e.g., gear, pulleys solenoids, etc.) to an closed position. To this end, each of the resilient ends 151a and 151b includes a radius of curvature "R" of suitable dimensions to accomplish a particular surgical purpose. Resilient ends 151a and 151b may also operably cooperate with one more additional springs disposed in the housing 20 to provide the necessary closure forces, e.g., the resilient ends 151a and 151b are configured to offload some of the required forces from a more transitional spring disposed in the housing 20.

With continued reference to FIGS. 2A and 2B, jaw members 110, 120 are shown. Jaw members 110 and 120 including respective jaw housings 117 and 127, and operative components associated therewith, may be formed from any suitable material, including but not limited to metal, metal alloys, plastic, plastic composites, and so forth. In the embodiment illustrated in FIGS. 2A and 2B, each of the jaw members 110 and 120 including respective housings 117 and 127 is formed from metal. Jaw members 110 and 120 are operatively and pivotably coupled to each other via a pivot pin 111 (or other suitable device). Respective electrically conductive seal plates 118 and 128 are operably supported on and secured to jaw housings 117 and 127 of respective the jaw members 110 and 120. More particularly, a distal end 117a and a distal end 127a of respective jaw members 110 and 120 may be configured to securely engage the respective electrically conductive seal plate 118 and 128 or, with respect to a monolithic jaw member, form the seal plates 118 and 128.

It should be noted that jaw members 110 and 120 and respective housings 117 and 127 are substantially identical to each other. In view thereof, and so as not to obscure the present disclosure with redundant information, the operative components associated with the jaw member 110 and jaw housing 117 that are operably associated with the drive mechanism 150 including wire 151 are described in further detail, and only those features distinct to jaw member 120 and jaw housing 127 will be described hereinafter.

Continuing with reference to FIGS. 2A and 2B, proximal end 117b of jaw housing 117 is disposed in an oblique orientation with respect to an axis "B-B" that is defined through the end effector 100. More particularly, axis "B-B" is substantially parallel to the longitudinal axis "A-A" that is defined through the shaft 12. Proximal end 117b may be disposed at any suitable angle, e.g., 0-90°, with respect to the axis "B-B." In the illustrated embodiment, proximal end 117b is oriented at approximately a 45° angle with respect to the axis "B-B." Disposing the proximal end 117b in an oblique orientation with respect to the axis "B-B" facilitates opening and closing the jaw members 110 and 120. Moreover, the angle may be adjusted to accommodate and/or achieve specific closure or sealing forces at the jaw member 110 and 120 when the jaw members are in the closed or clamping position, e.g., the greater the angle of the proximal end 117b with respect to the axis "B-B," the greater the closure force (for a given configuration of the distal end 152) when the jaw members 110 and 120 are in the clamping position.

In accordance with the present disclosure, jaw housings 117 and 127 include respective proximal ends 117b and 127b that operably couple to respective resilient ends 151a and distal end 151b of the split wire configuration to facilitate opening and closing in of the jaw members 110 and 120. More specifically, proximal end 117b is in operative communication with resilient end 151a of wire 151 such that proximal movement of the wire 151 causes one or both of the jaw members 110 and 120 to move from the open position (FIG. 1A) to the closed or clamping position (FIG. 1B). For example, in one particular embodiment, when the wire 151 is "pulled," i.e., moved or translated proximally, resilient end 151a and resilient end 151b are caused to move toward one another, which, in turn, causes both of the jaw members 110 and 120 to move toward one another. Alternatively, and if desired, the drive assembly 130 including the wire 151 and resilient ends 151a and 151b may be configured such that when the wire 151 is "pushed," i.e., moved or translated distally, both of the jaw members 110 and 120 are caused to move toward one another.

Proximal end 117b operably and securely couples to resilient end 151a of the wire 151 by any suitable method. In the illustrated embodiment, proximal end 117b includes an aperture 115 defined therein of suitable proportion that is dimensioned to operably couple to a distal tip 155 of the resilient end 151a. The distal tip 155 may be shaped to engage aperture 115. In the illustrated embodiment, the distal tip 155 is "hook" shaped to facilitate securement of the distal tip 155 within the aperture 115. In one particular embodiment, a bead of solder may be placed about aperture 115 of the proximal end 117b to ensure that the proximal end 117b and distal end 151a remain secured to each other during opening and closing sequences.

An opening 108 extends through a medial portion of the jaw housing 117b and is configured to receive pivot pin 111 (opening 108 is shown engaged with pivot pin 111 and as such is not explicitly visible). In the embodiment, illustrated in FIGS. 2A and 2B, opening 108 (and the pivot pin 111 housed therein) includes a generally circumferential configuration. In certain embodiments, pivot pin 111 is securely disposed to an internal frame associate with the shaft 12 and/or the end effector 100.

In an assembled configuration each of the jaw members 110 and 120 is positioned in side-by-side relation. Pivot pin 111 is positioned within the opening 108 associated with jaw member 110 and a corresponding opening (not explicitly shown) associated with jaw member 120. As noted above, the pivot pin 111 provides a point of pivot for each of the jaw members 110 and 120. The jaw members 110 and 120 may be pivotably supported at the distal end 14 of the shaft 12 by any suitable method, such as, for example, by the method described in commonly-owned U.S. Patent Application publication No. 2007/0260242, filed Jul. 11, 2007.

In use, initially jaw members 110 and 120 are biased in an open position under the force provided by the spring 153 formed by the resilient ends 151a and 151b (FIGS. 1A and 2A). Tissue is positioned between the jaw members 110 and 120. Proximal movement of the movable handle 40 "pulls" wire 151 proximally, which, in turn, causes the resilient ends 151a and 151b to move toward each other, this, in turn, causes the jaw members 110 and 120 to toward each other against the bias of spring 153 such that tissue is clamped between the jaw members 110 and 120 (FIGS. 1B and 2B). The configuration of the spring 153 (e.g., the radius of curvature "R" associated with each of the resilient ends 151a and 151b) generates a sealing or closure force at the jaw members 110 and 120. The combination of jaw members 110 and 120 including jaw housings 117 and 127 operably coupled to the wire 151 including resilient ends 151a and 151b provides a consistent, uniform tissue effect, e.g., tissue seal. Moreover, the frictional losses that are typically associated with conventional forceps when a drive rod is translated within a shaft are offloaded and/or diminished by the spring-like component 153 operably associated with the jaw members 110 and 120. In other words, it is irrelevant if the shaft 12 is bent or articulated since the biasing force of the resilient spring ends 151a and 151 located at the jaw members 110 and 120 will remain unaffected.

Figure 3A:
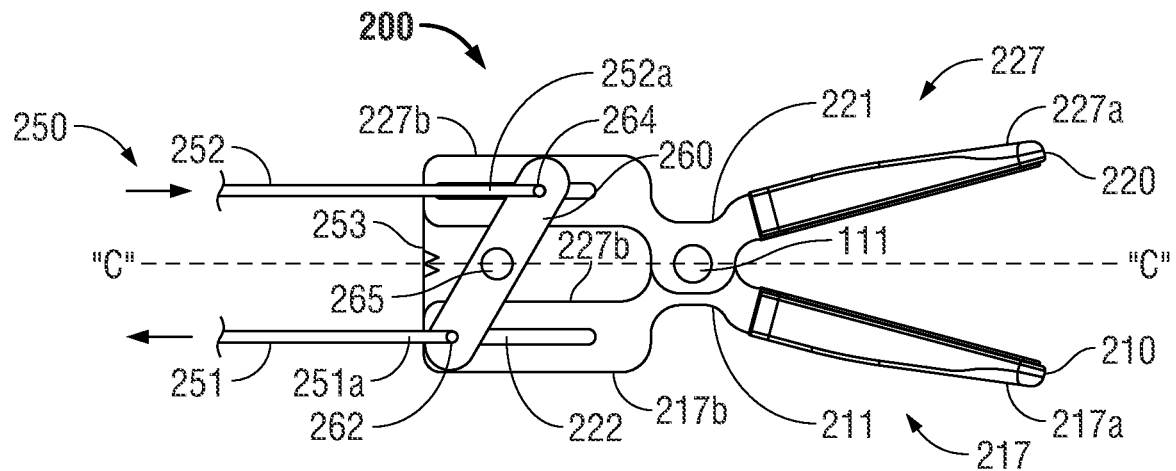
FIGS. 3A and 3B are schematic views of jaw members configured for use with the endoscopic forceps depicted in FIGS. 1A and 1B according to an alternate embodiment of the present disclosure.
Figure 3B:
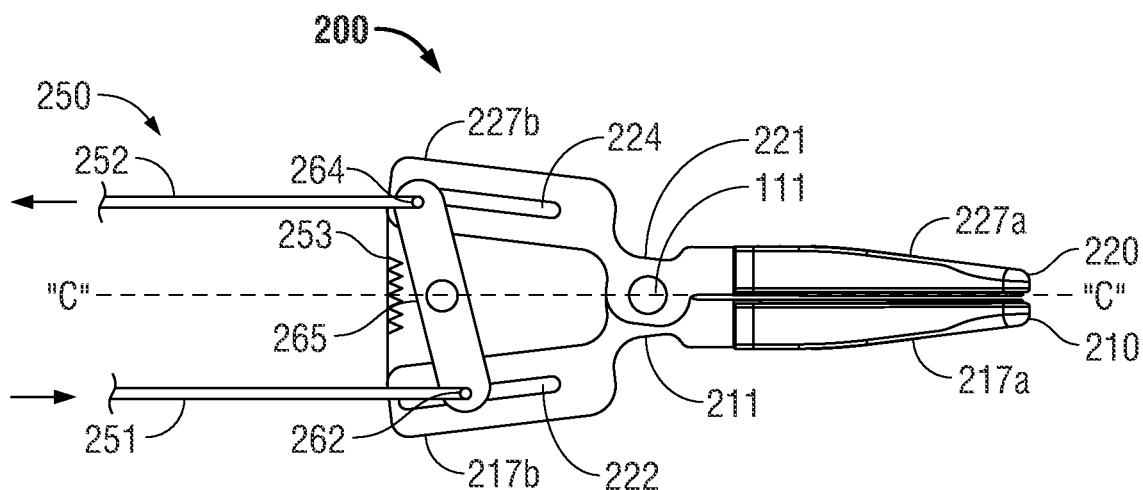

With reference to FIGS. 3A and 3B, an alternate embodiment of end effector 100 that is suitable for use with the bipolar forceps 10 depicted in FIGS. 1A and 1B is shown and end effector designated 200. End effector 200 includes two jaw members 210 and 220 that are similar to that of jaw members 110 and 120, respectively. Accordingly, only those features that are unique to jaw members 210 and 220 are discussed in further detail.

Each of jaw members 210 and 220 includes a respective cam slot 222 and 224 defined therein disposed on a respective proximal end 217b and 227b (FIGS. 3A and 3B) thereof. Each of the cam slots 222 and 224 is configured to operably couple to a center link 260 that is operably associated with each of the jaw members 210 and 220, described in greater detail below. Each of the cam slots 222 and 224 is disposed in a generally parallel configuration with respect to a longitudinal axis "C-C" that is parallel to the longitudinal axis "A-A."

As described above with respect to jaw members 110 and 120, jaw members 210 and 220 are pivotably coupled to each other via pivot pin 111.

A distinguishing feature of the jaw members 210 and 220 when compared to jaw members 110 and 120 is the generally "U" shaped medial portion 211 and 221 associated with each of the jaw members 210 and 220, respectively. The medial portions 211 and 221 provide a structural transition from a respective distal end 217a and 227a to the respective proximal end 217b and 227b of the jaw members 210 and 220 such that the respective proximal and distal ends 217a, 227a and 217b and 227b remain in substantial parallel alignment with respect to each other when the jaw members 210 and 220 are moved from the open to clamping position (see FIG. 3A in combination with 3B). The parallel alignment of the respective proximal and distal ends and center link 260 provides increased structural integrity to the jaw housings 217 and/or the jaw member 210 and facilitates the transfer of closure force to the jaw members 210 and 220 when the jaw members 210 and 220 are in the clamping position.

A drive mechanism 250 operably couples to the drive assembly 130 and is in operative communication with the end effector 200. Drive mechanism 250 is configured similar to that of drive mechanism 150. More particularly, drive mechanism 250 is operably associated with the drive assembly 130 and may be any suitable drive mechanism including but not limited to one or more flexible or resilient bands, cables, wires, etc. Similar to that of drive mechanism 150, the drive mechanism 250 is substantially flexible to accommodate bends typically associated with shaft 12 when the bipolar forceps 10 is positioned within a patient and when the jaw members 210 and 220 are being moved from an open configuration for positioning tissue between the jaw members, to a closed configuration for grasping tissue. With this purpose in mind, the drive mechanism 250 includes a split wire configuration having a pair of wires 251 and 252 disposed in substantial parallel relation with respect to each other and proportioned such that the wires 251 and 252 "bend" or "flex" when the wires 251 and 252 are pulled and/or pushed within the shaft 12.

Each of the wires 251 and 252 includes a proximal end (not explicitly shown) that is operably associated with the drive assembly 130 such that actuation of the movable handle 40 imparts movement of the jaw members 210 and 220.

Each of the wires 251 and 252 operably couples to a respective jaw member 210 and 220. More particularly, each of the wires includes a respective distal end 251a and 252a that operably couples to center link 260 which, in turn, operably couples to each of the jaw members 210 and 220, described in greater detail below.

In the embodiment illustrated in FIGS. 3A and 3B, the wires 251 and 252 are configured such that movement of one wire, e.g., wire 251, in a first direction, e.g., a proximal direction, causes movement of the other wire, e.g., wire 252, in a second direction, e.g., a distal direction, see FIGS. 3A and 3B, for example. Accordingly, when the movable handle 40 is moved, e.g., moved proximally, the wires 251 and 252 cause the jaw members 210 and 220 to move from the open position to the closed position (see FIGS. 3A and 3B).

Center link 260 operably couples to each of the jaw members 210 and 220 and is configured to move the jaw members 210 and 220 from the open configuration to the closed configuration when the movable handle 40 is move proximally. More particularly, center link 260 operably couples to cam slot 222 disposed on jaw member 210 and cam slot 224 disposed on jaw member 220 (see FIGS. 3A and 3B) via one or more coupling methods. More particularly, center link 260 includes a cam pin 262 that is operably disposed within the cam slot 222 and a cam pin 264 that is operably disposed within the cam slot 224. This cam pin and cam slot configuration facilitates proximal and distal movement or translation of the center link 260 when the movable handle 40 is moved proximally. Center link 260 is configured such that center link 260 is operably disposed in a generally oblique orientation with respect to the longitudinal axis "C-C" when the jaw members 210 and 220 are in the open position (FIG. 3A) and is disposed in a generally orthogonal orientation with respect to the longitudinal axis "C-C" when the jaw members 210 and 220 are in the closed position (FIG. 3B).

To facilitate movement of center link 260, an aperture (not explicitly shown) of suitable proportion is operably defined in center link 260 and is configured to securely engage a pivot pin 265 that is secured to an internal portion of the shaft 12 and/or end effector 200.

A resilient or "spring-like component" 253 (hereinafter simply referred to as spring 253) is operably associated with each of the jaw members 210 and 220 and is configured to bias the jaw members 210 and 220 in the open position such that tissue may be positioned between the jaw members 210 and 220. Moreover, the spring 253 and center link 260 collectively provide a closure force at the jaw members 110 and 120 that is in the range of about 3 kg/cm$^2$ to about 16 kg/cm$^2$ or about 120 pounds per square inch when the jaw members 210 and 220 are in the clamping position. Spring 253 is operably secured or coupled to a respective proximal end 217b and 227b of each of the jaw members 210 and 220 by any suitable securement or coupling methods. In the illustrated embodiment, the spring 253 is overmolded to each of the proximal ends 217b and 227b of the jaw members 210 and 220, respectively. Alternatively, spring 253 may be secured to the proximal ends 217b and 227b by one or more mechanical connections, e.g., rivet or pin. Spring 253 may be any suitable type of spring including but not limited to compression spring, torsion spring, leaf spring, etc. In the embodiment illustrated in FIGS. 3A and 3B, the spring 253 is a compression spring 253.

While the spring 253 has been described herein as being operably associated with the center link 260 to bias the jaw members 210 and 220 in the open position, it is within the purview of the present disclosure that the center link 260 function without the spring 253.

Operation of the bipolar forceps 10 with the end effector 200 is described. In use, initially jaw members 210 and 220 are biased in an opened position under the force provided by the spring 253 (FIG. 3A). Tissue is positioned between the jaw members 210 and 220, the movable handle 40 is moved proximally causing the wire 251 to move proximally and wire 252 to move distally. This proximal and distal movement of the wires 251 and 252, respectively, causes cam pins 262 and 264 of the center link 260 to translate in a corresponding direction within respective cam slots 222 and 224 against the bias of the spring 253, which, in turn, causes both of the jaw members 210 and 220 to move toward each other such that tissue is grasped between the jaw members 210 and 220 (FIG. 3B). The jaw housings 217 and 227 with center link 260 and spring 253 generate a sealing or closure force at the jaw members 210 and 220. This combination of jaw housings 217 and 227 with center link 260 and spring 253 provides a consistent, uniform tissue effect, e.g., tissue seal. Moreover, the combination of jaw housings 217 and 227 with center link 260 and spring 253 provides an additional mechanical advantage at the jaws 110 and 120. More particularly, the frictional losses that are typically associated with conventional forceps when a drive rod is translated within a shaft is offloaded and/or diminished by the spring 253 operably associated with the jaw housing 217 and 127.

Figure 4:
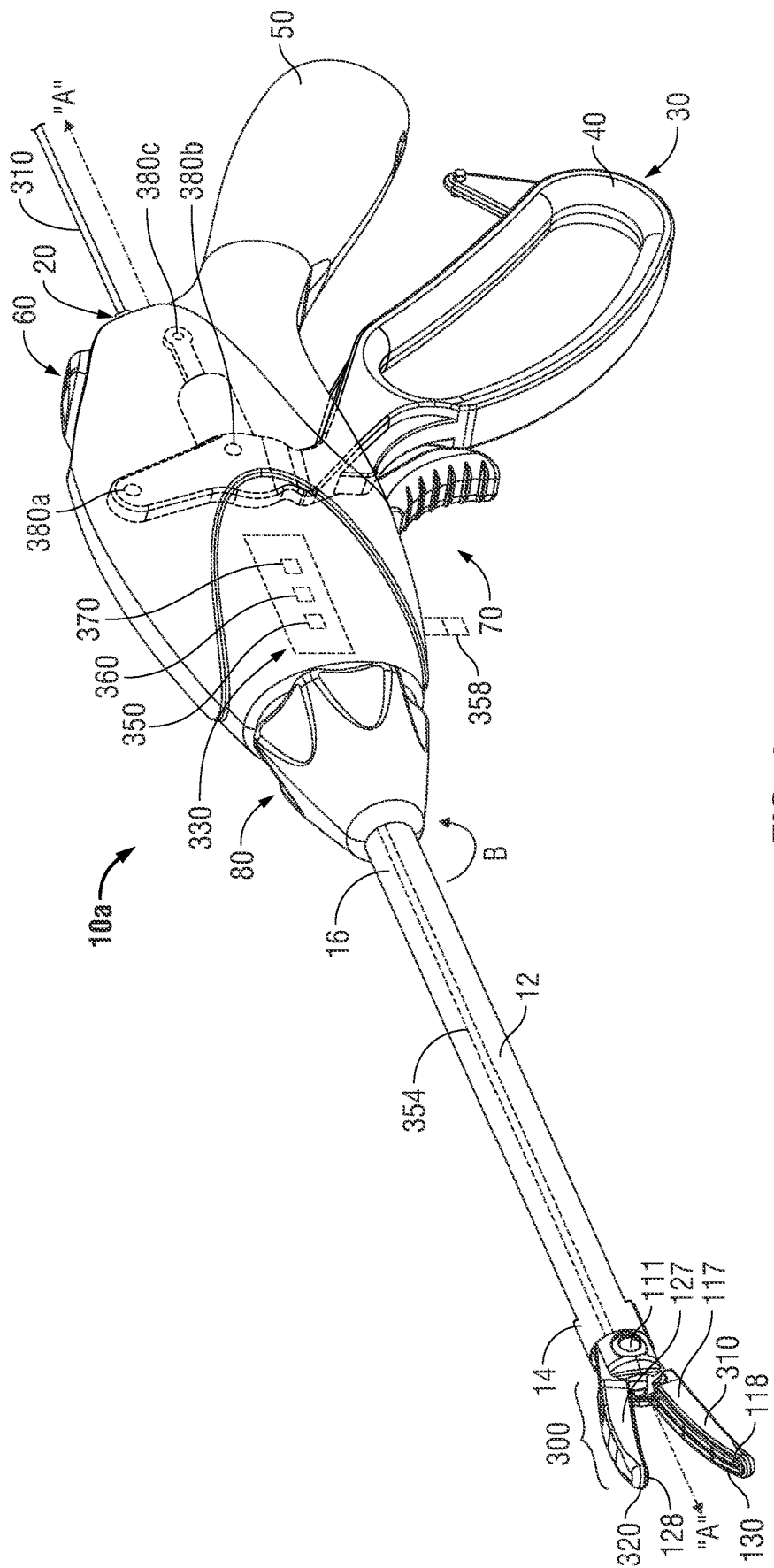
FIG. 4 is a side, perspective view of an endoscopic bipolar forceps showing an end effector assembly including jaw members according to an embodiment of the present disclosure.

With reference to FIG. 4, an alternate embodiment of the bipolar forceps 10 is shown designated 10a. Bipolar forceps 10a is similar to bipolar forceps 10. A distinguishing feature of bipolar forceps 10a when compared to bipolar forceps 10 is that a drive assembly 330 is disposed in operative communication with an end effector 300 via a hydraulic drive mechanism 350 (as best seen in FIGS. 5A and 5B), a pneumatic drive mechanism 360 and/or an electromechanical drive mechanism 370. In the embodiment illustrated in FIG. 4, drive assembly 330 may operably couple to the movable handle 40 via one or more suitable coupling methods. For example, in the illustrative embodiment, the movable handle 40 may operably couple to one (or combination thereof) of the aforementioned drive mechanisms, e.g., the hydraulic drive assembly 350, via one or more pivot pins. More particularly, a pivot pin 380a operably couples the movable handle 40 to an internal frame of the housing 20, a pivot pin 380b operably couples the movable handle 40 to the hydraulic drive mechanism 350 and a pivot pin 380c operably couples the hydraulic drive mechanism 350 to the internal frame of the housing 20, shown in phantom in FIG. 4. Drive assembly 330 is configured such that proximal movement of the movable handle 40 causes the drive assembly 330 (or operative component associated therewith) to engage and actuate one of the foregoing drive mechanisms (e.g., the hydraulic drive mechanism 350) that includes a biasing component such that jaw members 310 and 320 associated with the end effector 300 move from an open position to a closed position, described in greater detail below.

With reference now to FIGS. 5A and 5B, and initially with reference to FIG. 5A, hydraulic drive mechanism 350 (HDR 350), and operative components associated therewith, is illustrated. HDR 350 includes a main housing 352 that is operably disposed within the housing 20 of the bipolar forceps 10a and is in operative communication with the drive assembly 330 and fluid communication with end effector 300 including jaw members 310 and 320 via a hydraulic fluid line 354.

With continued reference to FIG. 5A, main housing 352 operably connects to an adjustment device 356. In the embodiment illustrated in FIG. 5A, the adjustment device 356 is supported by the main housing 352 and is configured to adjust a throw of the jaw members 310 and 320. That is, the adjustment device 356 is configured to control, inter alia, the amount of deflection or movement of the jaw members 310 and 320. To this end, a thumb screw 358 (or other suitable device) operably couples to the adjustment device 356. More particularly, thumbscrew 358 is operably disposed on an exterior of the housing 20 (shown for illustrative purposes in FIG. 5A) and is accessible to a user. In use, a user may rotate, e.g., either in a clockwise or counterclockwise direction, the thumbscrew 358 to achieve a specific amount of deflection or movement at the jaw members 310 and 320.

As noted above, drive assembly 330 engages the HDR 350. More particularly, a proximal end of the HDR 350 is dimensioned to movably retain a plunger 362 that is operably coupled to the drive assembly 330. Plunger 362 translates within the main housing 352 such that displacement of the plunger 362 within the main housing 352 causes a corresponding movement of the jaw members 310 and 320. The plunger 362 includes a plunger head 363 dimensioned to provide a fluid tight seal between the main housing 352 and the plunger head 363. This fluid tight seal maintains the pressure within the hydraulic fluid line 354 such that an optimum amount of deflection or movement is achieved for a given end effector.

A spring 364 is operably secured within the main housing 352 and is configured to control seal or closure pressure at the jaw members 310 and 320 when the jaw members are in the clamping position.

Hydraulic fluid line 354 couples to a distal end of the main housing 352 and is proportioned and dimensioned to couple to the end effector 300 including jaw members 310 and 320. Hydraulic line 354 may be made from any suitable material, e.g., a substantially flexible material, and extends within the shaft 12, shown in phantom in FIG. 4. Hydraulic fluid line 354 holds one or more suitable hydraulic fluids therein, e.g., saline, that provides the requisite pressure for closing and opening the jaw members 310 and 320. More particularly, as the movable handle 40 is moved proximally, the plunger 362 including plunger head 363 causes the hydraulic fluid to move within the hydraulic fluid line 354 such that the jaw members 310 and 320 move from the open position to the clamping position.

In one particular embodiment, a reservoir 368 is in fluid communication with the main housing 352 and is configured to automatically supply hydraulic fluid into the hydraulic fluid line 354, such as, for example, in the instance where the hydraulic fluid level falls below a predetermined level. To this end, a one-way valve 372 is in fluid communication with the reservoir 368 and the hydraulic fluid line 354. One-way valve 372 is operably disposed between the reservoir 368 and the hydraulic fluid line 354, as best seen in FIG. 5B. The combination of reservoir 368 and one-way valve 372 ensures that an specific working range of pressure is maintained within the hydraulic fluid line 354 such that a specific sealing or closure pressure (e.g., sealing or closure pressure approximately equal to 3 kg/cm$^2$ to about 16 kg/cm$^2$) is maintained at the jaw members 310 and 320 when jaw members 310 and 320 are in the clamping position.

For a more detailed description of hydraulic mechanism 350 (including operative components associated therewith), reference is made to commonly-owned U.S. patent application Ser. No. 12/211,205 filed on Sep. 16, 2008.

Figure 6A:
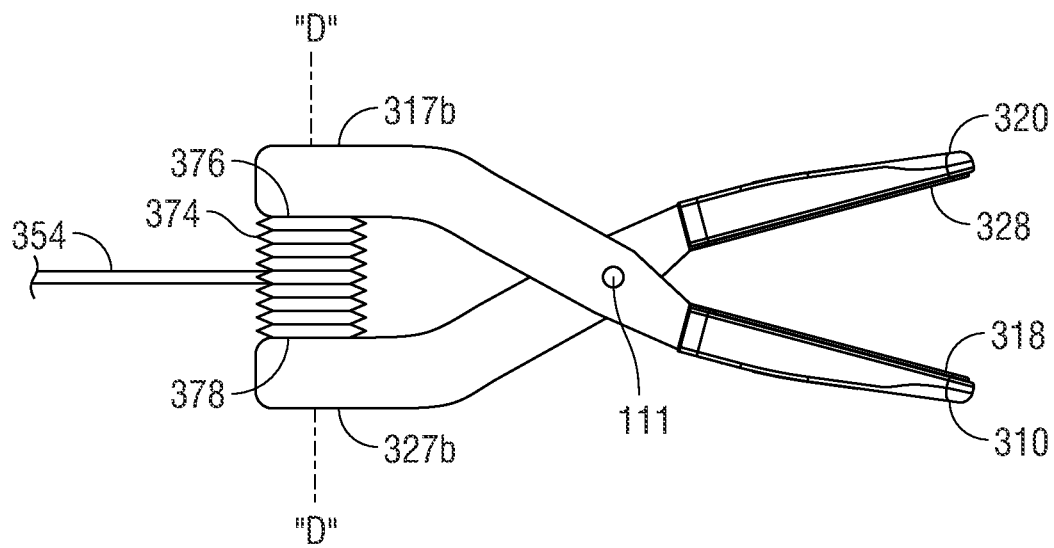
FIGS. 6A and 6B are schematic views of jaw members configured for use with the endoscopic forceps depicted in FIG. 4 according to another embodiment of the present disclosure.
Figure 6B:
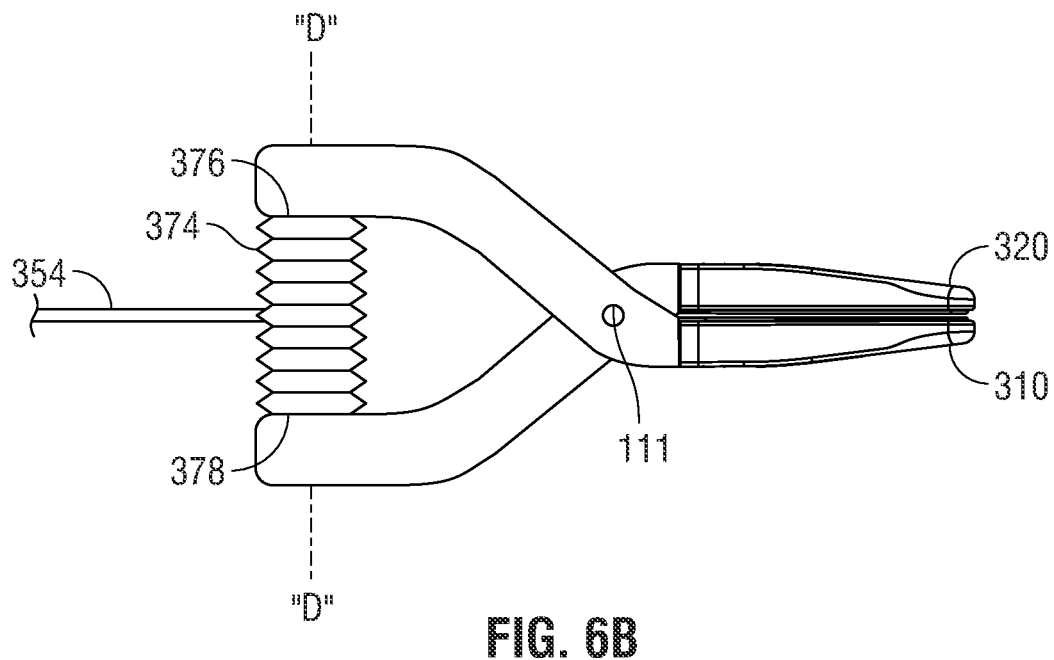

Turning now to FIGS. 6A and 6B, and initially with reference to FIG. 6A, end effector 300 including jaw members 310 and 320 configured for use with the bipolar forceps 10a is illustrated. Jaw members 310 and 320 are similar to that of jaw members 110 and 120, respectively. Accordingly, only those features that are unique to the operation of the bipolar forceps 10a and jaw members 310 and 320 are described in further detail.

A biasing component in the form of a bellows 374 of suitable proportion is operably coupled to and associated with each of the jaw members 310 and 320. More particularly, bellows 374 includes respective top and bottom portions 376 and 378 that are operably secured (by any suitable method) to proximal ends 317b and 327b, respectively. Bellows 374 is in fluid communication with the hydraulic fluid line 354 and is configured to store a quantity of the hydraulic fluid therein. Bellows 378 moves in a plane "D-D" that is orthogonal to the longitudinal axis "A-A" from a non-expanded or compressed condition or state wherein the jaw members 310 and 320 are in the open position (FIG. 6A) to an expanded or non-compressed condition wherein the jaw members 310 and 320 are in the clamping position (FIG. 6B).

Figure 7A:
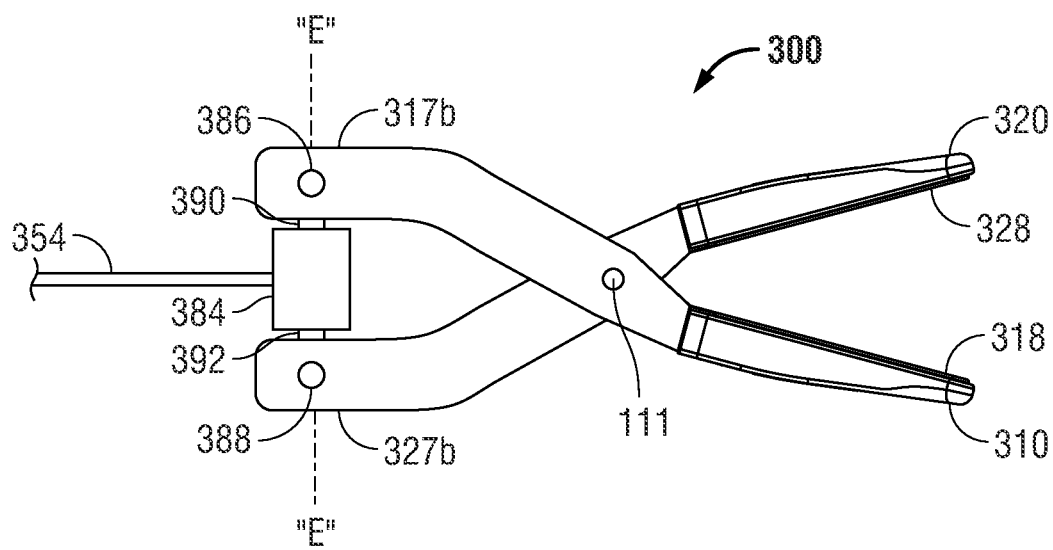
FIGS. 7A and 7B are schematic views of jaw members configured for use with the endoscopic forceps depicted in FIG. 4 according to yet another embodiment of the present disclosure.
Figure 7B:
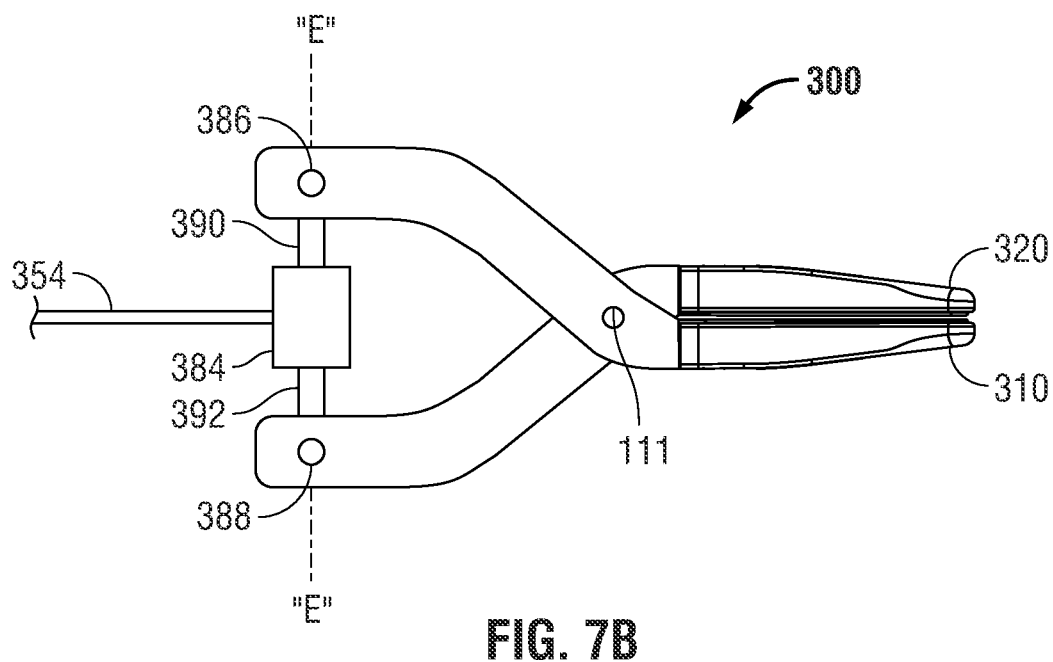

Referring to FIGS. 7A and 7B, and initially with reference to FIG. 7A, an alternate embodiment a biasing component configured for use with the jaw members 310 and 320 is illustrated and is in the form of a piston 384.

Piston 384 is of suitable proportion and operably couples to each of the jaw members 310 and 320. More particularly, piston 384 includes respective top and bottom portions 386 and 388 that are operably secured to proximal ends 317b and 327b, respectively. More particularly, top portion 386 of the piston 384 includes a crankshaft 390 that is operably coupled (by any suitable coupling method(s)) to the proximal end 317b of jaw member 310. Likewise, bottom portion 388 of the piston 384 includes a crankshaft 392 that is operably coupled (by any suitable coupling method(s)) to the proximal end 327b of jaw member 320. Piston 384 is in fluid communication with the hydraulic fluid line 354 and is configured to store a quantity of the hydraulic fluid therein. Crankshafts 390 and 392 of the piston 384 move in a plane "E-E" that is orthogonal to the longitudinal axis "A-A" from a non-expanded condition or state wherein the jaw members 310 and 320 are in the open position (FIG. 7A) to an expanded condition wherein the jaw members 310 and 320 are in the clamping position (FIG. 7B).

Operation of the bipolar forceps 10a with the end effector 300 is described. In use, initially jaw members 310 and 320 are biased in an opened position (see FIGS. 6A and/or 7A, for example). Once tissue is positioned between the jaw members 310 and 320, the movable handle 40 is moved proximally causing the drive assembly 330 to cause the plunger 362 to move distally within the main housing 352.

With respect to the embodiment illustrated in FIG. 6B, this distal movement of the plunger 362 causes the pressure in the hydraulic fluid line to build up, which, turn, causes the bellows 374 to move from the non-expanded condition to the expanded condition, which, in turn, causes both of the jaw members 310 and 320 to move toward each other such that tissue is grasped between the jaw members 310 and 320 (FIG. 6B).

Alternatively, and with respect to the embodiment illustrated in FIG. 7B, the distal movement of the plunger 362 causes the pressure in the hydraulic fluid line to build up, which, turn, causes the crankshafts 390 and 392 of the piston 384 to move from the non-expanded condition to the expanded condition, this, in turn, causes both of the jaw members 310 and 320 to move toward each other such that tissue is grasped between the jaw members 310 and 320 (FIG. 7B).

HDR 350 including bellows 374 or piston 384 is configured to generate the necessary sealing or closure force at the jaw members 310 and 320. The combination of movable handle 40 and HDR 350 including either bellows 374 or piston 384 provides a consistent, uniform tissue effect, e.g., tissue seal. Moreover, the combination of movable handle 40 and HDR 350 including either bellows 374 or piston 384 provides an additional mechanical advantage at the jaws 310 and 320. More particularly, the frictional losses that are typically associated with conventional forceps when a drive rod is translated within a shaft is offloaded and/or diminished.

Figure 8A:
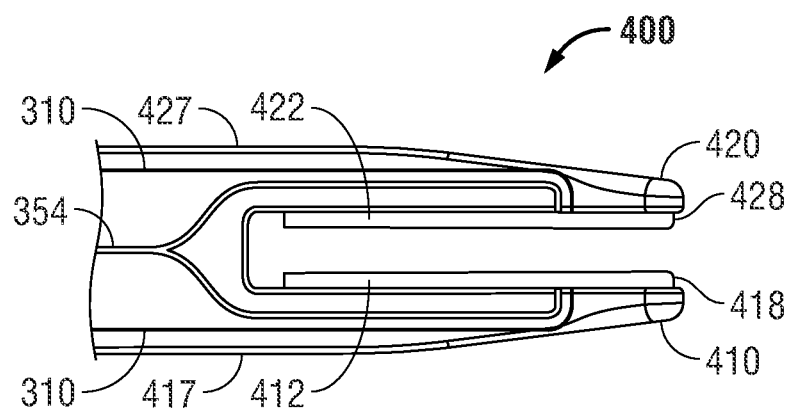
FIGS. 8A and 8B are schematic views of jaw members configured for use with the endoscopic forceps depicted in FIG. 4 according to still yet another embodiment of the present disclosure.
Figure 8B:
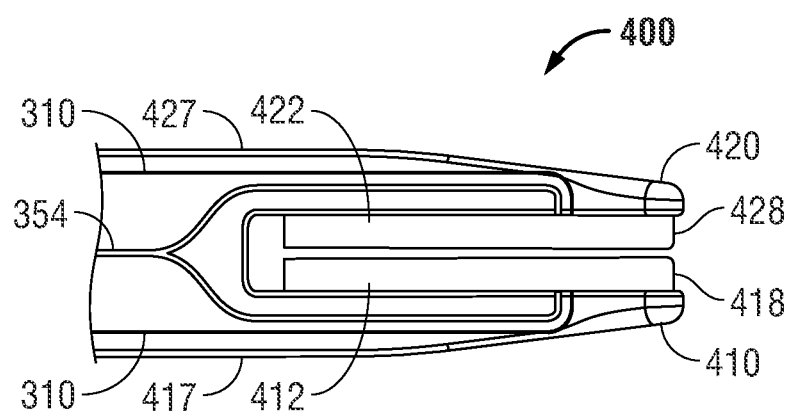

Turning now to FIGS. 8A and 8B, and initially with reference to FIG. 8A, an end effector 400 including jaw members 410 and 420 configured for use with the bipolar forceps 10*a* is illustrated. Jaw members 410 and 420 are similar to that of jaw members 110 and 120, respectively. Accordingly, only those features that are unique to the operation of the bipolar forceps 10*a* and jaw members 410 and 420 are described in further detail.

Each of the jaw members 410 and 420 includes a respective seal plate 418 and 428. A distinguishing factor of the jaw members 410 and 420 when compared to the previously described jaw members, e.g., jaw members 110 and 120, is that the seal plates 418 and 428 are movable with respect to a respective jaw housing 417 and 427. More particularly, in the embodiments illustrated in FIGS. 8A and 8B, after tissue is positioned between the jaw members 410 and 420, the seal plates 418 and 428 are caused to move toward each other such that a specific closure force is achieved at the seal plates 418 and 418 while the seal plates 418 and 428 are in the clamping position and tissue is grasped therebetween. To this end, each of the seal plates 418 and 428 are movably secured or coupled (via any suitable securement or coupling method) to a respective jaw member 410 and 420. In the illustrated embodiment, the jaw members 410 and 420 are fixedly secured to each other. That is, unlike the previously described jaw members, e.g., jaw members 110 and 120, jaw members 410 and 420 are not pivotably coupled to each other. In certain instances, however, the jaw members 410 and 420 may be pivotably coupled to each other, such as, for example, via one or more coupling methods previously described, e.g., via a pivot pin 111 that is associated with the end effector 400 and/or shaft 12.

Jaw members 410 and 420 include a respective heat activated, pneumatic activated, or hydraulic activated (or combination thereof) biasing component in the form of a bellows 412 and 422. In the embodiment illustrated in FIGS. 9A and 9B, the respective bellows 412 and 422 are operably positioned adjacent a respective seal plate 418 and 428. More particularly, the bellows 412 and 422 are operably positioned beneath the respective seal plate 418 and 428 and in operative communication with a respective driving mechanism, e.g., a hydraulic drive mechanism 350, a pneumatic drive mechanism 360 and an electromechanical drive mechanism 370.

In the instance where the bellows 412 and 422 are hydraulically activated, hydraulic mechanism 350 may be utilized to activate each of the bellows 412 and 422. More particularly, and in this instance, the hydraulic fluid line 354 may be operably disposed on each of the jaw members 410 and 420 and in fluid communication with a respective bellows 412 and 422. Accordingly, when the movable handle 40 is moved proximally, the respective bellows 412 and 422 on jaw members 410 and 420 expand, which, in turn, cause the respective seal plates to expand such that tissue is grasped therebetween and subsequently sealed.

In the instance where the bellows 412 and 422 are pneumatically activated, a pneumatic mechanism 360 may be utilized to activate each of the bellows 412 and 422. More particularly, and in this instance, a pneumatic fluid line (not shown) may be operably disposed on each of the jaw members 410 and 420 and in fluid communication with a respective bellows 412 and 422. Accordingly, when the movable handle 40 is moved proximally, the respective bellows 412 and 422 on jaw members 410 and 420 expand, which, in turn, causes the respective seal plates to expand such that tissue is grasped therebetween and subsequently sealed.

In the instance where the bellows 412 and 422 are heat-activated, an electromechanical mechanism 370 may be utilized to activate each of the bellows 412 and 422. More particularly, and in this instance, an electrical cable, e.g., cable 310, may be operably disposed on each of the jaw members 410 and 420 and in electrical communication with a respective bellows 412 and 422. Bellows 412 and 422 may be made from a shape memory alloy (Nitinol). More particularly, the bellows will have a cold forged state that corresponds to an expanded position. Accordingly, when a current is applied to the bellows 412 and 422, the bellows 412 and 422 "heat-up" and transition to the cold forged state, i.e., expanded condition, which, in turn, causes the respective seal plates to expand such that tissue is grasped therebetween and subsequently sealed.

Operation of the bipolar forceps 10*a* with the end effector 400 is described. For illustrative purposes, operation of bipolar forceps 10*a* including end effector 400 is described in terms of use with HDR 350.

In use, initially jaw members 410 and 420 are in a substantially open position (see FIG. 8A). Tissue is positioned between the jaw members 410 and 420 including their respective seal plates 418 and 428, the movable handle 40 is moved proximally causing the drive assembly 330 to cause the plunger 362 to move distally within the main housing 352. This distal movement of the plunger 362 causes the pressure in the hydraulic fluid line to build up, which, in turn, causes the bellows 412 and 422 to expand. The bellows 412 and 422 move from the non-expanded condition to the expanded condition such that tissue is grasped between the jaw members 310 and 320 (FIG. 6B).

HDR 350 (including bellows 412 and 422) is configured to generate the necessary sealing or closure force at the jaw members 410 and 420. The combination of movable handle 40 and HDR 350 (including bellows 412 and 422) provides a consistent, uniform tissue effect, e.g., tissue seal. Moreover, the combination of movable handle 40 and HDR 350 provides an additional mechanical advantage at the jaw members 410 and 420. More particularly, the frictional losses that are typically associated with conventional forceps when a drive rod is translated within a shaft is offloaded and/or diminished. An advantage of jaw members 410 and 420 that utilize respective bellows 412 and 422, when compared to conventional jaw members, is that the bellows 412 and 422 conform to tissue disposed between the jaw members 110 and 120.

From the foregoing and with reference to the various figure drawings, those skilled in the art will appreciate that certain modifications can also be made to the present disclosure without departing from the scope of the same. For example, other spring mechanisms such as, for example, foam, spring washers, and so forth, may be operably associated with any of the aforementioned configurations of end effectors including their respective jaw members, e.g., end effector 100 including jaw members 110 and 120, and utilized to generate a closure or sealing force at the jaw members.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical tissue sealing device, comprising:
   a housing;
   a shaft extending from the housing and defining a longitudinal axis;
   first and second jaw members coupled to a distal end portion of the shaft and movable between an open position and a clamping position, each of the first and second jaw members defining a cam slot;
   a drive assembly including two cables, the drive assembly extending from within the housing through the shaft, the two cables configured to move longitudinally within the shaft to impart movement of the first and second jaw members;
   a center link coupled to a respective distal end of the two cables; and
   a pair of cam pins extending from the center link and disposed within the respective cam slots of the first and second jaw members, wherein longitudinal movement of the two cables within the shaft causes the pair of cam pins to translate within the respective cam slots to move the first and second jaw members between the open and clamping positions.

2. The electrosurgical tissue sealing device according to claim 1, further comprising a torsion spring configured to impart a closure force on the first and second jaw members.

3. The electrosurgical tissue sealing device according to claim 2, wherein the closure force on the first and second jaw members is in the range of about 3kg/cm$^2$ to about 16 kg/cm$^2$.

4. The electrosurgical tissue sealing device according to claim 1, wherein each of the first and second jaw members includes a seal plate configured to deliver electrosurgical energy to tissue.

5. The electrosurgical tissue sealing device according to claim 1, wherein the pair of cam pins extends from opposing sides of the center link.

6. An electrosurgical tissue sealing device, comprising:
   a housing;
   a shaft extending from the housing and defining a longitudinal axis;
   first and second jaw members coupled to a distal end portion of the shaft and movable between an open position and a clamping position;
   two cables extending through the shaft, the two cables configured to impart movement of the first and second jaw members;
   a center link coupled to a respective distal end of the two cables; and
   a cam pin extending from the center link and disposed within a cam slot defined by one of the first or second jaw members, wherein longitudinal movement of the two cables causes the cam pin to translate within the cam slot to move the first and second jaw members between the open and clamping positions.

7. The electrosurgical tissue sealing device according to claim 6, further comprising a torsion spring configured to impart a closure force on the first and second jaw members.

8. The electrosurgical tissue sealing device according to claim 7, wherein the closure force on the first and second jaw members is in the range of about 3 kg/cm$^2$ to about 16 kg/cm$^2$.

9. The electrosurgical tissue sealing device according to claim 6, wherein each of the first and second jaw members includes a seal plate configured to deliver electrosurgical energy to tissue.

10. An electrosurgical tissue sealing device, comprising:
    a housing;
    a shaft extending from the housing and defining a longitudinal axis;
    first and second jaw members coupled to a distal end portion of the shaft and movable between an open position and a clamping position, each of the first and second jaw members defining a cam slot;
    a drive assembly extending from within the housing through the shaft, the drive assembly including two elongate drive members configured to move longitudinally within the shaft to impart movement of the first and second jaw members;
    a center link coupled to a respective distal end of the two elongate drive members; and
    a pair of cam pins extending from the center link and disposed within the respective cam slots of the first and second jaw members, wherein longitudinal movement of the two elongate drive members within the shaft causes the pair of cam pins to translate within the respective cam slots to move the first and second jaw members between the open and clamping positions.

11. The electrosurgical tissue sealing device according to claim 10, wherein the two elongate drive members are substantially parallel and spaced-apart relative to one another.

12. The electrosurgical tissue sealing device according to claim 10, wherein the two elongate drive members include cables.

13. The electrosurgical tissue sealing device according to claim 10, wherein each of the first and second jaw members includes an electrically-conductive surface configured to deliver electrosurgical energy to tissue.

14. The electrosurgical tissue sealing device according to claim 10, wherein the pair of cam pins extends from opposing sides of the center link.

15. The electrosurgical tissue sealing device according to claim 10, further comprising a torsion spring configured to impart a closure force on the first and second jaw members.

16. The electrosurgical tissue sealing device according to claim 10, wherein the two elongate drive members are flexible.

17. The electrosurgical tissue sealing device according to claim 10, wherein the shaft is configured to articulate.

18. The electrosurgical tissue sealing device according to claim 10, wherein the two elongate drive members are configured to move longitudinally within the shaft in opposite directions.

19. The electrosurgical tissue sealing device according to claim 10, wherein the center link is configured for pivotable movement in response to longitudinal movement of the two elongate drive members.

* * * * *